United States Patent [19]

Weiss

[11] Patent Number: 4,545,658

[45] Date of Patent: Oct. 8, 1985

[54] VISUAL EXAMINATION APPARATUS

[76] Inventor: Joseph F. Weiss, 8425 Countrywood Fairway, Cordova, Tenn. 38018

[21] Appl. No.: 468,067

[22] Filed: Feb. 22, 1983

[51] Int. Cl.⁴ .............................................. A61B 3/02
[52] U.S. Cl. .................................... 351/222; 351/243
[58] Field of Search ............... 351/222, 237, 239, 243, 351/233, 221

[56] References Cited

U.S. PATENT DOCUMENTS

| | | | |
|---|---|---|---|
| 2,232,316 | 2/1941 | Deederer | 351/243 X |
| 2,239,164 | 4/1941 | Wigelsworth | 351/222 X |
| 2,247,653 | 7/1941 | Feldman | 351/243 X |
| 2,283,769 | 5/1942 | Schwanzel | 351/222 X |
| 3,684,355 | 8/1972 | Molner | 351/221 X |

Primary Examiner—Rodney B. Bovernick
Attorney, Agent, or Firm—John J. Mulrooney

[57] ABSTRACT

A visual examination apparatus for administering a photostress recovery test. The photo pigments of the cones of the subject eye are conditioned to a steady state by exposure to a dim light which retro-illuminates an optotype. The size of the optotype is related to the visual acuity of the subject eye. A bright light source of repeatable duration and intensity and spectral distribution of energy is directed to bleach the photo pigments of the cones of the macula. A common switch triggers the flash and starts a digital timer. After the flash, a different optotype of the same size as the initial one is substituted therefor. When the subject eye recovers from the dazzling flash sufficiently to detect the different optotype, the timer is stopped. The length of time required for the cones of the macula to regenerate photo pigment is dependent upon whether the cones are normal and on their apposition to the retinal pigment epithelium. The recovery time period indicates a normal or abnormal condition of the cones of the macula.

4 Claims, 4 Drawing Figures

VISUAL EXAMINATION APPARATUS

BACKGROUND OF THE INVENTION

1. Field of the Invention

The present invention relates generally to visual examination apparatus and, more particularly, to an apparatus for examining the eye of a human being by administering a standardized bleaching flash of light to a subject's eye and measuring the photostress recovery time required for the cones of the macula to recover from the exposure to the bright light.

2. Description of the prior art

The retina is the perceptive structure of the human eye and consists of several layers upon which light falls and makes an impression. For practical purposes the retina can be considered to be divided into layers of nerve cells and their fibers. The deepest layer is made up of rods and cones. This is the part of the retina which is sensitive to light. In the central portion of the retina is a small area called the macula which lies in the visual axis of the eye. The fovea of the macula is the point of greatest sensitivity within the retina, and vision of any considerable accuracy is limited to this small area.

The rods and cones are light-sensitive cells. The cones are concentrated in the central portion of the macula (fovea) and are more diffusely scattered in the periphery. There are no rod cells at the fovea which is the area of distinct vision. In the peripheral portions of the retina, outside the macula, there are both rods and cones, with rods alone at the periphery. The outer segments of the rods and cones contain photopigment which changes with the amount of illumination. The rod cells are concerned with peripheral vision and vision in dim illumination (night vision). The cones are involved vision in bright light, vision requiring high spatial discrimination, and color vision. It has been shown that some cones absorb maximally at 440 mm (blue cones), some at 540 mm (green cones), and some at 560 mm (red cones).

It has been known for some time in the art of visual examination that prolonged decrease in visual acuity occurs in a patient with central serous retinopathy after examination with an opthalmoscope. It is also a part of the prior art that a method or test for central serous retinopathy can be performed by (1) determining the best visual acuity of the eye, (2) exposing the eye to the light of an opthalmoscope for approximately fifteen seconds and (3) measuring the time period required for the vision to return to the pre-test level. This method or test is referred to as the photostress recovery test and the time period required for the vision to return to the pre-test level is called the photostress recovery time. The photostress recovery test has been used to diagnose various maculopathies.

Presently, there is no visual examination apparatus capable of reliably testing the recovery of foveal cone pigments after exposure to a bleaching light. The photostress test as heretofore administered by holding an available bleaching light source relatively close to the subject's eye to expose the eye to the light for an period of time and then measuring by a watch the time required for the subject's visual acuity to return to a predetermined level is inexact at best.

The principle disadvantage in this present method of administering the photostress test is the lack of standardization. The intensity of the dazzling light, the duration of the exposure and the distance between the light source and the eye are all variable. The accuracy of fixation of the dazzle light on the fovea, the possibility of the subject blinking and random eye movements are not controllable. Because of this lack of standardization in the photostress test as presently administered, the method is inconvenient and unreliable and, consequently, infrequently used. It requires a physician or a trained individual to administer the test and cannot be used for serious clinical investigation.

SUMMARY OF THE INVENTION

It is therefore an object of the present invention to provide a convenient and practical apparatus for performing a photostress test on a human eye.

It is a further object of the present invention to provide an apparatus for administering a standardized photostress test to the human eye.

It is a further object of the present invention to provide a apparatus for administering a photostress test to a human eye whereby photostress recovery times between normal and abnormal eyes may be easily distinguished.

In accordance with the present invention, a visual examination apparatus useful for administering the photostress to a human eye is provided. The photo pigments of the cones of the subject eye are conditioned to a predetermined steady state by exposure to a dim light which retro-illuminates an optotype. The size of the optotype is chosen to be two lines better than the visual acuity of the eye, e.g., if the vision is 20/20 an optotype of 20/30 size is used. Line refers to the lines on a standard Snellen chart. A bright light source of repeatable energy and duration, such as a xenon flash, is used to bleach the photo pigments of the cones of the macula. The xenon flash starts a digital timer. After the flash, a different optotype of the same size as the initial one is substituted therefor. When the subject eye recovers from the dazzling flash sufficiently to detect the different optotype, the timer is stopped. The length of time required for the cones of the macula to regenerate photo pigment is dependent upon whether the cones are normal and on their apposition to the retinal pigment epithelium. The relative length or shortness of the recovery time period indicates a normal or abnormal condition of the cones of the macula.

Among the advantages of the present invention are an apparatus capable of performing a standardized photostress test by delivering the same amount of light for the same duration on each test. The apparatus provides for the proper fixation of the dazzle light on the cones of the fovea, and since the flash is very brief, problems of blinking and eye movement are reduced to a minimum. The apparatus of the present invention provides a photostress tester which is convenient and easy to use even by non-medical personnel after only a few minutes instruction. The standardization of the photostress test by the present invention enables the present invention to be used for serious clinical investigation. The present invention also allows spectral photostress testing to be done so that the condition of red, green or blue cones can be selectively studied.

DESCRIPTION OF THE PREFERRED EMBODIMENTS

Figure 1:
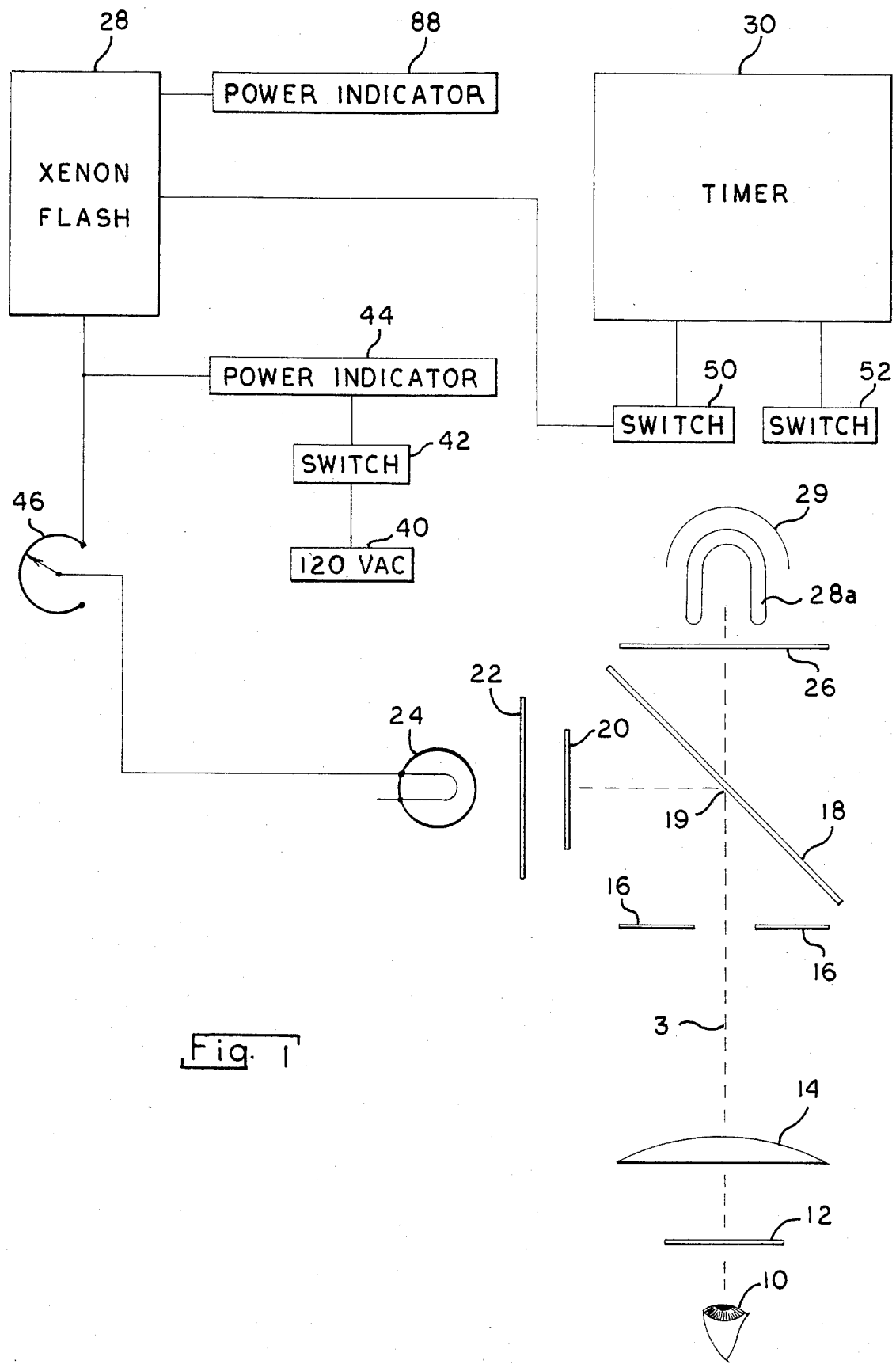
FIG. 1 is a schematic diagram of the visual examination apparatus illustrating the basic operative functions of a preferred embodiment of the present invention.

Referring now to the drawings, wherein like reference characters designate corresponding parts throughout the several figures, there is illustrated in FIG. 1 a schematic diagram of the visual examination apparatus of the present invention. The schematic diagram shows the positioning of the eye 10 to be tested with respect to the viewing assembly comprising a narrow band pass filter 12, a positive 4 diopter meniscus lens 14, a baffle 16, a beam splitter 18, an optotype slide 20 having first and second Landalt rings (FIG. 2) thereon, an opal diffusing glass 22, and a 5-watt lightbulb 24. A diffuser 26 and a xenon flash unit 28 are aligned with the visual axis 3 of subject eye 10, so that when the subject observes the optotype the eye observes the reflection of the optotype on the beam splitter at point 19 the visual axis of the eye will be aligned with the xenon flash to insure bleaching of the fovea. A digital timer 30 is connected to be actuated when the xenon unit flashes.

The visual examination apparatus of the present invention will be housed in a convenient cabinet (not shown) having an opening therein for the eye to view the optotype and to be bleached by the xenon flash. The housing will have a control panel comprising switch means 42, 50, 52 (FIG. 3), a power indicator 44, slot means by which the optotype slide 20 may be changed, a window for viewing the read out on the digital timer 30, an arm control for potentiometer 46, and an indicator that the capacitors are charged 88.

Figure 2:
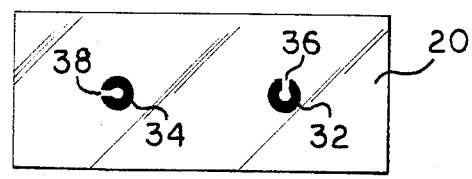
FIG. 2 is a front elevation view of the optotype slide.

FIG. 2 is a front elevation view of one embodiment of the optotype slide 20 having first and second Landalt rings 32 and 34 thereon. In the illustrated embodiment, the slide is made of clear acrylic having black optotypes thereon. An alternative embodiment is to provide a slide having a black surface with clear optotypes thereon. The gap width 36 and 38 and line width of the Landalt rings are approximately one-fifth (1/5th) of the height of the optotypes. The size of the optotypes is determined by the subject's visual acuity, and a plurality of slides each having a different size of optotype thereon is contemplated.

In the use of the visual examination apparatus of the present invention, the subject eye to be tested is positioned to observe a Landalt ring on the optotype slide 20, which is retroilluminated through the opal diffusing glass 22 by the 5-watt bulb 24. The positive diopter meniscus lens 14 assists the eye in focusing on the Landalt ring, and the baffle 16 provides an apperture to define the area to be viewed. The beam splitter 18 functions as a mirror for the subject to view the Landalt ring. The photo pigments of the cones of the macula adjust to a predetermined steady state while focusing on the Landalt ring. This provides a standardized condition of photopigments before the bleaching light is administered.

The xenon flash unit 28 is aligned with the visual axis 3 extending from the eye 10 to the horseshoe xenon bulb 28. While the eye views the optotype, the xenon flash unit 28 is triggered. Simultaneously, a brilliant dazzling flash from the xenon light causes bleaching of the photo pigments of the photo recepters of the eye and the digital timer 30 is started. The diffusing screen 26 prevents a distinct after-image of the xenon bulb on the retina of the subject eye and results in a diffuse after-image instead. Before the eye recovers to the state of pretest bleaching, the Landalt ring viewed by the subject eye is changed by moving the slide 20. When the subject eye has recovered sufficiently to correctly identify the location of the gap 36 or 38 in the Landalt ring, the timer is stopped. The elapsed time is the photostress recovery time and is useful as an indicator of the normal or abnormal condition of the cones of the macula.

Figure 3:
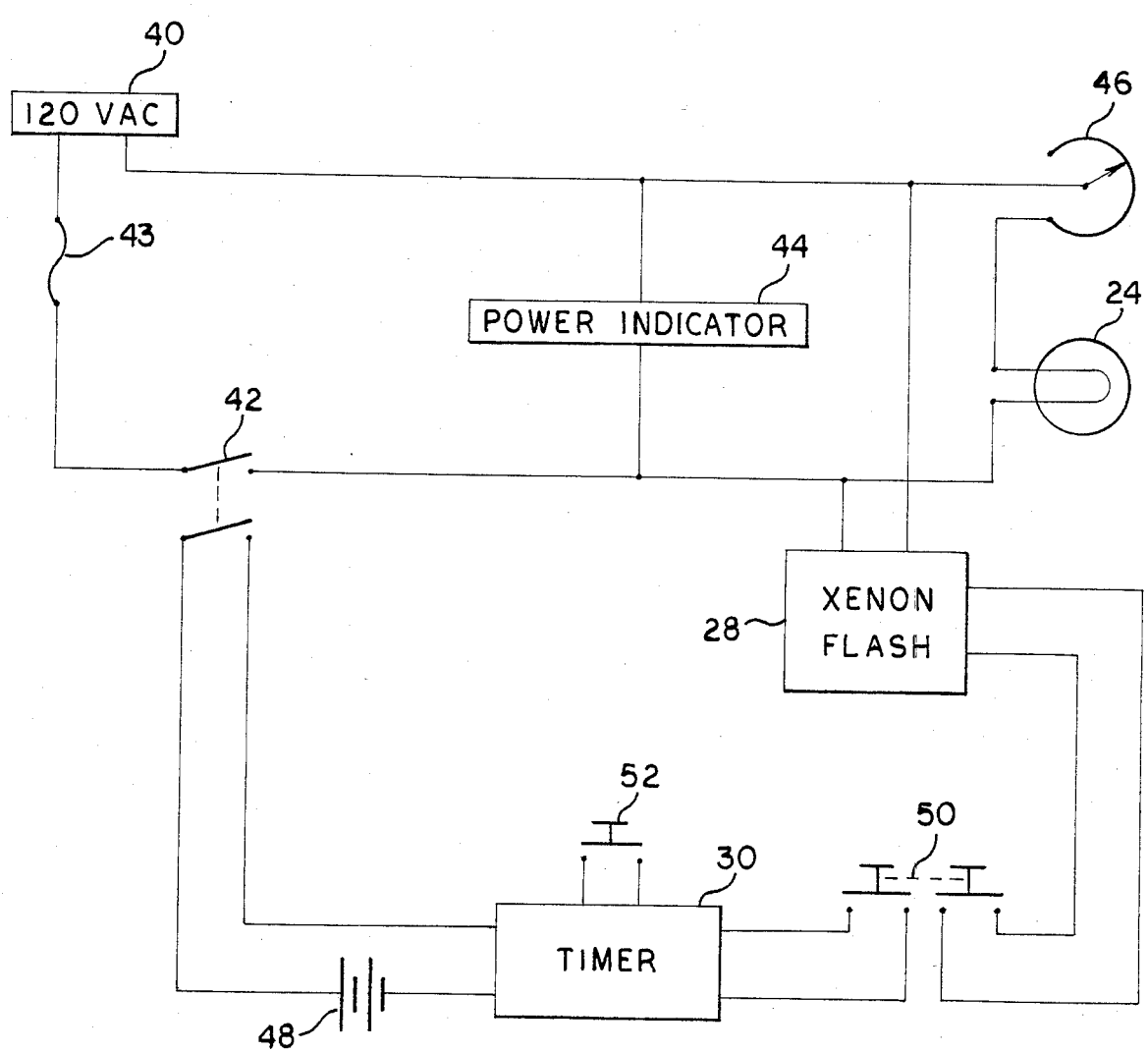
FIG. 3 is a schematic wiring diagram of the visual examination apparatus for the present invention.

Referring now to FIG. 3, there is illustrated a general schematic wiring diagram of the visual examination apparatus of the present invention. The circuit is energized through input plug 40 by on-off power switch 42. A power indicator 44 is connected to the input source (not shown) via fuse 43 and visually indicates when the apparatus is turned on. A rotary type potentiometer 46 as described below is connected in series with the 5-watt bulb 24. The xenon flash unit 28 is connected in the circuit with the timer 30 and a DC battery 48. A single throw-four pole switch 50 functions to simultaneously trigger the xenon flash unit 28 and start the timer 30. A switch 52 functions to stop the timer and reset the timer.

Figure 4:
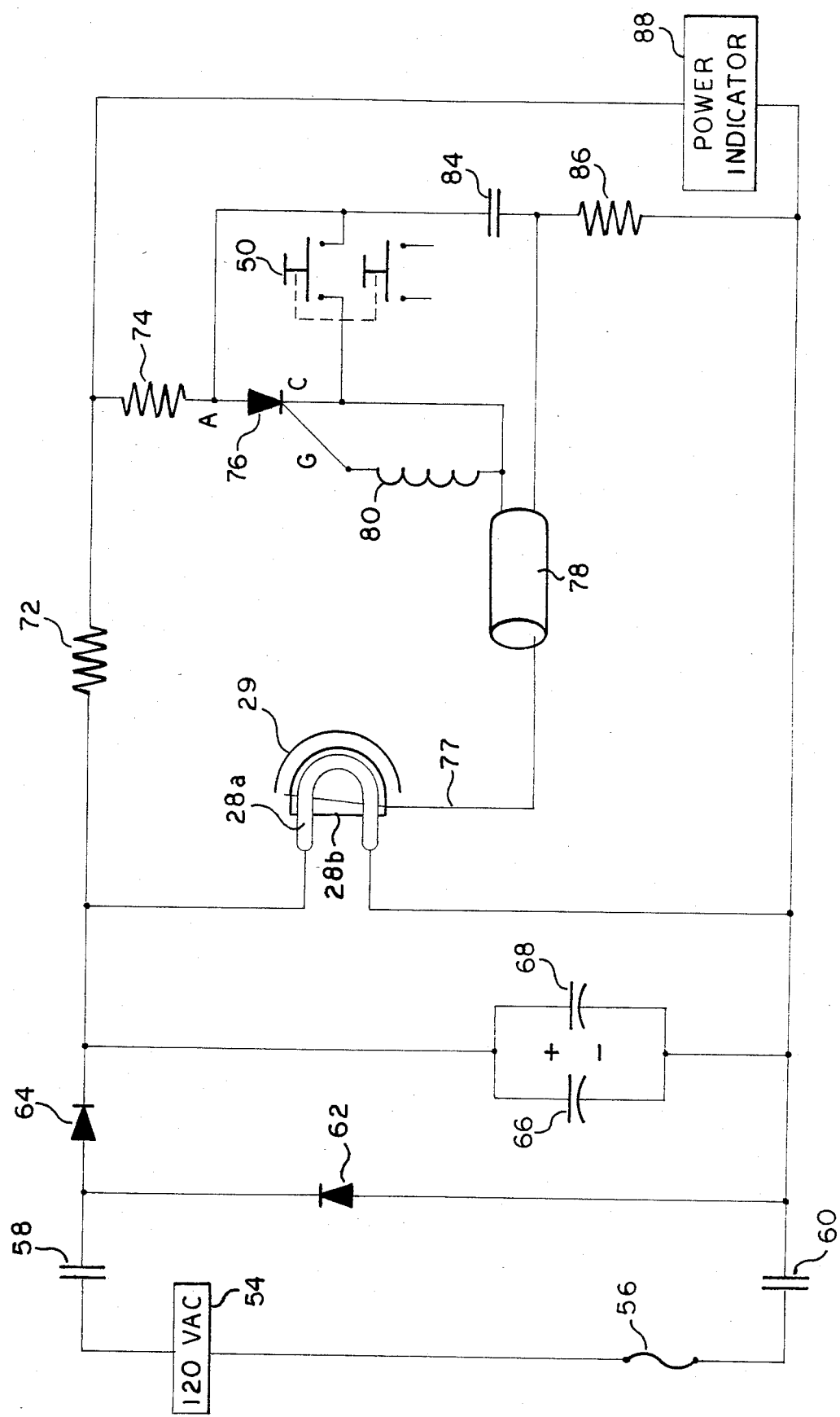
FIG. 4 is a schematic wiring diagram of the xenon flash unit of the visual examination apparatus of the present invention.

Referring now to FIG. 4, there is illustrated a wiring diagram for one preferred embodiment of the xenon flash unit 28. The circuit comprises a connection 54 to a standard source of 120 VAC power. The circuit comprises a fuse 56, capacitors 58 and 60, a first diode 62 and a second diode 64, a third capacitor 66 and a fourth capacitor 68, a xenon horseshoe flash tube 28a, housed within a metal flashtube holder bracket 28b, a reflector 29, a first resistor 72 and a second resistor 74, an SCR 76, a trigger coil 78 and a pulse transformer 80, the switch 50, a fifth capacitor 84, a third resistor 86 and a green dot neon tube 88. A wire 77 extends from trigger coil 78 and is inserted between and contacts flashtube 28a and holder bracket 28b.

In using the present invention to perform a photostress test the power switch 42 allows the apparatus to be energized as indicated by the neon power indicator 44. The power turns on the 5-watt bulb 24 and charges the capacitors 66 and 68 of the xenon flash unit 28 which cause neon light 88 to glow. The eye 10 to be tested looks through the lens 14, through the apperture in baffle 16 and, by reflection from the beam splitter 18, onto a Landalt ring, either 32 or 34, on the clear optotype slide 20. The 5-watt bulb 24 is regulated by potentiometer 46 to deliver exactly 5 foot candles of light, which is diffused by the opal diffuser 22, to retro-illuminate the aligned Landalt ring on the slide 20. While the subject eye is fixated on the Landalt ring, the operater uses switch 50 (FIG. 3) to simultaneously flash the xenon flash unit 28 and start the digital timer 30. The xenon flash is diffused by diffusion screen 26 and passes through beam splitter 18, baffle 16, lens 14 and filter 12 to enter the eye 10 and bleach the photo pigments of the eye. While the photo pigments are regenerating, the ends of the slide 20 are reversed to change the Landalt ring viewed by the subject. If spectral testing is being done, the proper filter 12 is then placed between the eye 10 and lens 14, and the potentiometer is adjusted to deliver 5 foot candles of illuminating light to the eye. When the subject is able to locate the position of the gap in the optotype, the timer is stopped by the operator using switch 52. The elapsed time which is displayed on the digital timer is the photostress recovery time.

One embodiment of the present invention utilizes a rotary type potentiometer 24. In this modification, as illustrated in FIGS. 1 and 3, a filter holder (not shown) (440 mm, 532 mm or 560 mm) and a plurality of selectively insertable narrow band pass filters 12 are positioned in the viewing system between the subject eye 10 and the lens 14. The knob of the rotary potentiometer is marked to indicate clear or white light, red (560 mm), green (532 mm) and blue (440 mm) light. The light received at the lens 14 is adjusted by potentiometer 46 so that the subject eye is exposed to five foot candles of illuminating light regardless of which filter is used. The appropriate filter 12 is positioned in the filter holder and the rotary potentiometer is adjusted to the position corresponding to the selected color. This permits testing the red, green or blue cones individually.

While certain representative embodiments and details have been shown for the purpose of illustrating the invention, it will be apparent to those skilled in this art that various changes and modifications may be made therein without departing from the spirit or scope of the invention.

I claim:

1. Visual examination apparatus for administering the photostress recovery test to a human eye comprising:

a movable transparent slide having first and second Landalt rings selected with reference to the visual acuity of said eye imprinted thereon;

means comprising a variable light source and a diffuser positioned between said variable light source and said slide for retro-illuminating said slide to a predetermined level;

means comprising a lens and a beam splitter positioned relative to the visual axis of said eye to focus the view of said eye upon one of the Landalt rings;

means aligned with the visual axis of said eye for repeatedly producing and directing a brilliant flash of light having a spectral distribution including blue, green and red for bleaching the foveal cones of said eye;

a timer; and switch means for simultaneously triggering said flash means and starting said timer and for stopping and resetting said timer.

2. The visual examination apparatus of claim 1 wherein said flash means comprises a xenon horseshoe flash tube.

3. The visual examination apparatus of claim 1 further comprising filters positioned along said visual axis between the eye and said flash means to provide for spectral photostress testing.

4. The visual examination apparatus of claim 1 wherein said movable slide comprises a black surface having transparent optotypes thereon.

* * * * *